United States Patent [19]

Nivière et al.

[11] 4,039,519

[45] Aug. 2, 1977

[54] BROAD SPECTRUM ANTIBIOTICS AND METHOD

[75] Inventors: Pierre Nivière, Montlouis; Gérard Orillard, Vanves; Jean Blum, Courbevoie, all of France

[73] Assignee: Chimie & Biologie, Colombes, France

[21] Appl. No.: 567,751

[22] Filed: Apr. 14, 1975

[51] Int. Cl.$^2$ .................... C07C 103/52; A61K 37/00
[52] U.S. Cl. ............................ 260/112.5 R; 424/177
[58] Field of Search .................. 260/112.5 R; 424/177

[56] References Cited
PUBLICATIONS

Niviere: Chem. Abstr., 78:115225e, (1973).
Hamada et al., J. of Antibiotics, 23, pp. 170–171, (1970).

*Primary Examiner*—Delbert R. Phillips
*Attorney, Agent, or Firm*—McDougall, Hersh & Scott

[57] ABSTRACT

The present invention relates to the new antibiotic polymyxine methyl tetracycline wide spectrum salts of the general formula $$[(TH^+-CO-NH-CH_2-NH)_n-P, nA^=], m\ HB^-$$

in which $m$ and $n$ represent positive integers of less than 6, $A^=$ and $B^-$ represent mineral or organic anions, T represents an antibiotic residue of the tetracycline family of the formula $T-CO-NH_2$, P represents a polypeptidic antibiotic residue of the polymyxine family of the formula $P-(NH_2)_n$, and particularly tri(oxytetracycline methyl) colistine trichloride-sulfate. The present invention also relates to the methods of preparing antibiotic salts by preparing the methylols of tetracycline salts by the addition of formol to the tetracycline salts, then, with or without isolation of this intermediate product, condensing it with an antibiotic of the polymyxine family. The present invention also relates to medications and pharmaceutical forms containing the products of the invention.

2 Claims, No Drawings

BROAD SPECTRUM ANTIBIOTICS AND METHOD

The present invention relates to salts of polymyxine methyl tetracyclines having the characteristic formula (A):

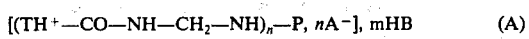

in which:

$m$ and $n$ represent positive integers less than 6, $A^-$ and $B^-$ represent mineral or organic amines, T represents a tetracyclical antibiotic residue of the tetracycline family of the formula $T-CO-NH_2$, such as tetracycline, oxytetracycline, dimethylchlorotetracycline, methacycline, rolitetracycline, doxycycline, minocycline, P represents a polypeptidic antibiotic residue of the polymyxine family, such as the A, B or E polymyxines or colistine.

The tritetracycline methyl polymyxine trichlorohydrates have previously been described, but they are not usable industrially because of their instability both in dry condition and in solution.

The salts of this invention are remarkable in that they are stable in dry condition and even in neutral or slightly alkaline solution, for example at pH 8.5.

The present invention also relates to products responding to the above formula (A) to trioxytetracycline methyl colistine trichlorohydrate, hereinafter called Negafongine.

The present invention also relates to the methods for the preparation of new salts of the invention, characterized by initially producing methylol from a salt of an antibiotic of the tetracycline family and by causing a polymyxine in salt to react in a suitable milieu.

According to the invention, a reaction medium is selected both for the initial addition and for the final condensation which does not react with formol, and although this temperature is not characteristic of the invention, generally the operation is carried out between room temperature and 60° C. In fact, above this temperature, the antibiotic substrata commence to degrade.

The present invention moreover relates to medications usable in human or veterinary medicine, characterized by containing, as primary or secondary active principal, one or more salts of the invention of the above formula (A). In fact, at variable doses, these compounds are bacteristatic, bacteriocides on the Gram+ and Gram− bacteria, and on the large viruses, the protozaires and certain flagellates.

The interest in the salts of formula (A) of the invention resides particularly in the fact that the toxicity of the polymyxines is considerably reduced in this type of compound and that the anti-bacterial activity of the new compounds of the invention is higher, in vitro and in vovo, than the simple mixture of antibiotics from substrates for the synthesis of the new salts of the invention. In vivo, in particular, it is surprising to note that the new salts of the invention completely pass the gastro-intestinal barrier, thus pass into the interior medium and thus make it possible to treat Gram− affections outside the digestive tract, such as urinary affections, while it is well known that tetracyclines, which pass the gastro-intestinal barrier, although poorly, are inactive and that the polymyxines do not pass this barrier and thus cannot act outside the digestive tract when they are administered orally.

The present invention relates in particular to medications for human or veterinary medicine, characterized by the fact that their activity is antibiotic and that they contain at least one salt of this invention of formula (A) above as primary or secondary active principal.

Moreover, the present invention relates to the pharmaceutical compounds containing at least one salt of the invention of above formula (A).

In addition, the present invention relates to the pharmaceutical forms, such as wafers, powders, gellules, compresses, lozenges, syrup for oral administration, to the form for administration in ophthalmology, otorhinolaryngology, such as drops, pommades, cones, to the forms of rectal administrations, suppositories, enemas, to ready to use injectable forms or those to be prepared at the time of use.

The invention will be better understood from the following example given as a non-limitative case and describing the preparation and properties of one of the sales of the invention, defined above under the name of Negafongine.

PREPARATION OF NEGAFONGINE 56 grams oxytetracycline chlorohydrate is put into suspension in 6 liters of pure anhydrous alcohol. Heat to 50° C and introduce, under agitation, 20 cc formol, previously concentrated by one third and filtered to eliminate the insolubles. The dissolution is complete in 15-20 minutes. Then evaporate to dryness under vacuum.

The crystals obtained are taken up with 50 cc absolute methanol after expansion in the air for a few hours to eliminate the formol odor. Add directly to this solution, 50 grams colistine sulfate to avoid the formation of lumps. Heat to 45°-50° C under agitation. The dissolution is complete in 10-15 minutes. Some insoluble flakes are filtered and the filtrate is left to stand overnight at −10° C. The Negafongine obtained is dried cold. 15-20% of product is still found in the mother liquors.

The Negafongine is water-soluble in stable form but has no clearly determined melting point because it decomposes when hot.

Spectroscopic-Analyses, performed essentially in comparison with those of the substrate having been used during the synthesis, that is to say oxytetracycline chlorohydrate and colistine sulfate.

Infrared Analysis by dispersion in Nujol.

Considerable differences exist between Negafongine and oxytetracycline chlorohydrate in the area of 3500-3000 $cm^{-1}$. Particularly the tetracyclinical band at 3400 $cm^{-1}$ no longer appears in Negafongine, which proves that the $-NH_2$ group of the oxytetracycline amide function has reacted, which is still confirmed, although this area is charged by differences observed in the region of 1700-1600 $cm^{-1}$.

Analysis by Nuclear Magnetic Resonance: by dissolution in deuterized dimethyl sulfoxide.

The spectrum of Negafongine has a mass in the strong fields which is absent in each of the starting substrate. It corresponds to the alcoyl radical hydrogens, proving the reality of the new Negafongine structure. In the region of the aromatic process, Negafongine maintains unchanged the oxytetracycline phenolhydroxyl, which implies that the addition of formol was not made in this area.

TOXICITY OF NEGAFONGINE

DL 50 per os male mice: 1900 mg/kg

DDL 50 intravenously male mice: 22.5 mg/kg

DL 50 intramuscular male mice: 125 mg/kg

These toxicological studies were completed by work on different galenic forms: "dry-fill" by intramuscular injection, "dry-fill" by intravenous injection, ready to use injectable solution, gelatin-coated pill for oral use, going from acute toxicity to chronic toxicity in mice, rats, rabbits and dogs. At doses 2.5 times higher than those provided in man, the tolerance always has been perfect, but at doses still 10 times higher, that is 25 times higher than those provided in man, a high mortality rate is observed (40% in rats 63 days after treatment), a relatively high reduction of the number of red blood corpuscles and rather severe gastric seizures also were noted.

ACTIVE ANTI-MICROBIAN ACTIVITY IN VITRO OF NEGAFONGINE

On Gram+ and Gram− bacteria of hospital origin, tests were conducted according to the known wells and disc method (gelatin medium). The activities of the colistine and of oxytetracycline are found with a synergizing activity which manifests itself particularly on the Aeruginose P.S. (Gram −).

Results of the Clinical Tests

The first clinical tests regarding Negafongine were conducted by oral administration (gelatin-coated pills at 250 mg), by intramuscular ready to use injection or "dry-fill", by intravenous injection. These results are perfectly satisfactory, particularly as far as oral administration is concerned, where it is known that the colistine cannot pass the gastro-intestinal barrier. In fact, negafongine proved to be active orally on Gram− affection of the respiratory, the urinary and the gynecological tracts, and of course the digestive track.

I claim:

1. The compound trioxytetracycline methyl cholistine trichlorohydrate and its salts.

2. -Tri-(oxytetracycline methyl) colistine trichlorohydrate-sulfate.

* * * * *